(12) United States Patent
Davidsen et al.

(10) Patent No.: US 10,743,840 B2
(45) Date of Patent: Aug. 18, 2020

(54) ULTRASOUND TRANSDUCER ASSEMBLY AND METHOD FOR TRANSMITTING AND RECEIVING ULTRASOUND WAVES

(71) Applicant: KONINKLIJKE PHILIPS N.V., Eindhoven (NL)

(72) Inventors: Richard Edward Davidsen, Eindhoven (NL); Junho Song, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 427 days.

(21) Appl. No.: 15/024,065

(22) PCT Filed: Sep. 15, 2014

(86) PCT No.: PCT/IB2014/064510
§ 371 (c)(1),
(2) Date: Mar. 23, 2016

(87) PCT Pub. No.: WO2015/044827
PCT Pub. Date: Apr. 2, 2015

(65) Prior Publication Data
US 2016/0213351 A1 Jul. 28, 2016

Related U.S. Application Data

(60) Provisional application No. 61/883,432, filed on Sep. 27, 2013.

(30) Foreign Application Priority Data

Nov. 8, 2013 (EP) ..................................... 13192121

(51) Int. Cl.
*A61B 8/00* (2006.01)
*B06B 1/02* (2006.01)
(Continued)

(52) U.S. Cl.
CPC ............ *A61B 8/4494* (2013.01); *A61B 8/145* (2013.01); *A61B 8/54* (2013.01); *A61B 8/56* (2013.01);
(Continued)

(58) Field of Classification Search
None
See application file for complete search history.

(56) References Cited

U.S. PATENT DOCUMENTS 8,248,889 B2 * 8/2012 Okuno ................. A61B 8/4444
367/180
8,475,382 B2 7/2013 Miyama et al.
(Continued)

FOREIGN PATENT DOCUMENTS

JP 2008136725 A 6/2008
WO 2013072803 A1 5/2013

*Primary Examiner* — Jonathan Cwern

(57) ABSTRACT

An ultrasound transducer assembly (10) is disclosed comprising a plurality of transducer elements (32) for transmitting and receiving ultrasound waves (24) each having a substrate (40) and a flexible membrane (46) disposed in a distance from a substrate. An AC voltage control unit (56) is provided for controlling an AC voltage provided to each of the transducer elements, and a DC voltage control unit (60) for controlling a DC bias voltage provided to the transducer elements in order to bring the flexible membranes in a collapse mode into contact with the substrate. The DC voltage control unit is adapted to disconnect the DC bias voltage from the transducer elements temporarily during the operation of the ultrasound transducer assembly to limit the collapse mode.

17 Claims, 5 Drawing Sheets

(51) Int. Cl.
 *G01S 15/89* (2006.01)
 *G01S 7/52* (2006.01)
 *A61B 8/14* (2006.01)

(52) U.S. Cl.
 CPC .......... *B06B 1/0207* (2013.01); *B06B 1/0223* (2013.01); *B06B 1/0292* (2013.01); *G01S 7/5202* (2013.01); *G01S 7/52025* (2013.01); *G01S 15/8915* (2013.01)

(56) References Cited

U.S. PATENT DOCUMENTS

| | | |
|---|---|---|
| 2005/0119575 A1 | 6/2005 | Ladabaum |
| 2007/0140515 A1 | 6/2007 | Oliver |
| 2010/0286527 A1* | 11/2010 | Cannon .................... A61B 7/04 600/459 |
| 2012/0194107 A1* | 8/2012 | Kandori ............... B06B 1/0292 318/116 |
| 2013/0088118 A1 | 4/2013 | Ho |

* cited by examiner

ULTRASOUND TRANSDUCER ASSEMBLY AND METHOD FOR TRANSMITTING AND RECEIVING ULTRASOUND WAVES

This application is the U.S. National Phase application under 35 U.S.C. § 371 of International Application No. PCT/IB2014/064510, filed on Sep. 15, 2014, which claims the benefit of U.S. Provisional Application No. 61/883,432 filed Sep. 27, 2013 and EP 13192121.5 filed Nov. 8, 2013. These applications are hereby incorporated by reference herein.

FIELD OF THE INVENTION

The present invention relates to an ultrasound transducer assembly and a method for transmitting and receiving ultrasound waves by an ultrasound transducer assembly. In particular, the present invention relates to an ultrasound imaging unit comprising capacitive micro-machined ultrasound transducer elements for emitting and receiving ultrasound waves and for providing ultrasound images.

BACKGROUND OF THE INVENTION

Capacitive micro-machined ultrasound transducer (CMUT) are a well-known technology for the use in ultrasound imaging applications and provide a possibility for a low-cost replacement of ultrasound transducers based on piezoelectric technology.

CMUT cells comprise a cavity underneath a flexible membrane. For detecting ultrasound waves, a vibration of the flexible membrane, which move or vibrate according to the receiving ultrasound waves, can be detected by measuring a variation of the capacitance between electrodes of the flexible membrane and a substrate of the CMUT cells. Conversely, an electrical signal applied to the electrodes of the CMUT cells cause the membrane to vibrate and thereby to emit ultrasound waves.

To increase the sensitivity of the CMUT cells, a "collapse mode" has been developed, wherein a DC bias voltage is used to bring the membrane into contact with the CMUT substrate and whereby the sensitivity of the cells can be doubled. A collapsed mode operable CMUT including a contoured substrate is e.g. known from US 2011/0040189 A1.

However, the CMUT cells operated in the collapse mode are subjected to electric charging and dielectric breakdown, whereby the lifetime of the CMUT cells is significantly reduced. Improved CMUT structures have been developed which can be operated in the collapse mode with high sensitivity having a longer dielectric life time, however, it has to be assured that the dielectric components of the CMUT cells do not charge or breakdown during the life time of the ultrasound transducers.

From US 2007/0140515 A1 a transducer static discharge apparatus is known, wherein light is exposed to capacitive membrane transducer elements of an ultrasound transducer assembly in order to reduce the static charge inside the transducer elements.

From US 2005/0119575 A1 a capacitive microfabricated transducer array for 3-D imaging is known, comprising a relatively large elevation dimension and a bias control of the elevation aperture in space and time.

From US 2012/0194107 A1 a control apparatus for a capacitive electromechanical transducer is known comprising cells each including first and second electrodes facing each other via a gap, a driving/detecting unit and an external stress applying unit, wherein the driving/detecting unit causes the second electrode to vibrate and to transmit elastic waves by generating an AC electrostatic attractive force between the electrodes, or to detect a charge of capacity between the electrodes, wherein the charge is caused by the second electrode vibrating upon receipt of elastic waves.

SUMMARY OF THE INVENTION

It is therefore an object of the present invention to provide an ultrasound transducer assembly having a high sensitivity and an improved life time. It is further an object of the present invention to provide an ultrasound imaging unit having a high sensitivity and an improved life time. Finally, it is an object of the present invention to provide a method for transmitting and receiving ultrasound waves by an ultrasound transducer assembly having a high sensitivity and an improved life time.

According to one aspect of the present invention, an ultrasound transducer assembly is provided comprising:
  a plurality of transducer elements for transmitting and receiving ultrasound waves each having a substrate and a flexible membrane disposed in a distance from a substrate,
  an AC voltage control unit for controlling an AC voltage provided to each of the transducer elements,
  a DC voltage control unit for controlling a DC bias voltage provided to the transducer elements in order to bring the flexible membranes in a collapse mode into contact with the substrate,
wherein the DC voltage control unit is adapted to disconnect the DC bias voltage from the transducer elements temporarily during the operation of the ultrasound transducer assembly to limit the collapse mode.

According to another aspect of the present invention, an ultrasound imaging unit is provided comprising an ultrasound transducer assembly for emitting and receiving ultrasound waves according to the present invention.

According to still another aspect of the present invention, a method for transmitting and receiving ultrasound waves by an ultrasound transducer assembly is provided comprising the steps of:
  providing an AC voltage to a plurality of transducer elements each having a substrate and a flexible membrane disposed in a distance to the substrate,
  providing a DC bias voltage to the plurality of transducer elements in order to bring the flexible membranes in a collapse mode into contact with the substrate, and
  disconnecting the DC bias voltage temporarily during operation of the ultrasound transducer assembly to limit the collapse mode.

Preferred embodiments of the invention are defined in the dependent claims. It shall be understood that the claimed method has similar and/or identical preferred embodiments as the claimed device and as defined in the dependent claims.

The present invention is based on the idea to reduce the time, during which the transducer cells are in the collapse mode and during which the flexible membrane is in contact with the substrate. Since the dielectric breakdown of the transducer cells occurs when a conductive path is formed through a dielectric layer when the flexible membrane is in contact with the substrate, the life time can be increased if the time during which the flexible membrane is in contact with the substrate is reduced or limited. According to the present invention, the DC bias voltage, which initiates the collapse mode and brings the flexible membrane into contact with the substrate is disconnected from the transducer cells in order to reduce the collapse mode time during the operation of the ultrasound transducer assembly. Hence, the ultrasound transducer elements can be operated with high sensitivity in the collapse mode and the life time of the transducer elements is increased since the time during which the transducer elements are operated in the collapse mode is reduced.

In a preferred embodiment, the DC voltage control unit is adapted to limit the collapse mode to a predefined time period. In particular, the DC voltage control unit is adapted to disconnect the DC bias voltage from the transducer elements after the predefined time period is reached and reconnects the DC bias voltage to the transducer elements as desired. By means of a time limit of the collapse mode, the time during which the flexible membrane is in continuous contact to the substrate can be limited so that the life time of the transducer elements can be improved.

In a preferred embodiment, the DC voltage control unit is adapted to limit the collapse mode on the basis of a temperature of the transducer elements. In particular the DC voltage control unit is adapted to disconnect the DC bias voltage from the transducer elements when a predefined temperature of the transducer elements is reached. By considering the temperature of the transducer elements, which is a further life time influencing parameter, can be limited.

In a preferred embodiment, the DC voltage control unit is adapted to disconnect the DC bias voltage from the transducer elements between transmitting and receiving of ultrasound waves by the transducer elements. This is a simple possibility to interrupt the collapse mode in a dead time of the transducer elements between a transmission mode and a receiving mode.

In a preferred embodiment, the ultrasound transducer assembly further comprises a transducer including the transducer elements and a main frame including a DC voltage supply. This is a possibility to provide a flexible use of the ultrasound transducer assembly.

It is further preferred, if a DC voltage control unit is integrated in a connector connecting the main frame and the transducer. This is a possibility to reduce the technical effort, since the DC bias voltage can be easily switched off by disconnecting the transducer from the DC voltage supply in the main frame.

In a further preferred embodiment, the DC voltage control unit is integrated in the main frame. This is a simple possibility to integrate the DC bias voltage supply and the DC voltage control unit, which can be easily controlled by a central processing unit in the main frame.

According to a preferred embodiment, the main frame and the transducer are separated and electrically connected to each other via a connection wire. This is a simple possibility to provide the electrical connection between the main frame and the transducer for driving the transducer elements.

In a preferred embodiment, the transducer elements are arranged in an array of transducer elements and the array is controlled by a control unit for ultrasound imaging. This is a preferred possibility to provide ultrasound imaging with low technical effort.

In a preferred embodiment, the DC voltage control unit is adapted to disconnect the DC bias voltage from the transducer elements in an imaging mode between transmitting and receiving of ultrasound waves. This is a simple possibility to interrupt the collapse mode in a dead time during the imaging scan to increase the life time of the transducer elements.

It is further preferred if the DC voltage control unit is adapted to disconnect the transducer elements in the imaging mode after receiving ultrasound waves and before transmitting ultrasound waves. This is an effective possibility to increase life time, since a dead time between receiving and transmitting during the imaging scan can be a comparable long dead time of the transducer elements.

In a preferred embodiment, the DC voltage control unit is adapted to disconnect the DC voltage from the transducer elements while the control unit stores image data received from the transducer array. This is a further possibility to reduce the time of the collapse mode and to increase the life time of the transducer elements since the dead time of the transducer elements during storing the image data can be effectively used.

In a preferred embodiment, the DC voltage control unit is adapted to disconnect the transducer elements while the control unit receives data for controlling the transducer array. In particular the control unit receives or downloads control data like digital beam forming data, steering data or set up data for the ultrasound transducer elements during which the DC voltage control unit disconnects the transducer elements from the DC bias voltage. This is a further possibility to limit the collapse mode effectively with low technical effort, since the dead time of uploading control data can be used.

In a preferred embodiment, the DC voltage control unit is adapted to disconnect the transducer elements after a predefined control signal free time period. This is a possibility to switch the collapse mode off, when the transducer in not in use. Hence, the transducer elements can be switched in a stand by mode when no control signal has been received from the input device after a predefined time period.

In a preferred embodiment, the ultrasound transducer assembly comprises a contact measurement unit for detecting a contact of the transducer to an object, wherein the DC voltage control unit is adapted to disconnect the transducer elements while the transducer is disconnected from the object. This is a possibility to restrict the collapse mode to the time during which the transducer is used to transmit ultrasound waves to an object and/or to receive ultrasound waves from an object to be measured.

As mentioned above, the present invention can effectively increase the life time of the transducer elements, since the time of the collapse mode can be effectively reduced by disconnecting a DC bias voltage from the transducer elements, wherein the sensitivity of the transducer assembly is high due to the use of the collapse mode. Since the dead time of the transducer assembly is used for switching the collapse mode off, in particular during imaging scans, the life time can be increased without reducing the functionality of the transducer assembly. Further, the life time can be improved since the most significant wear-out influence values like time duration of the collapse mode is considered.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
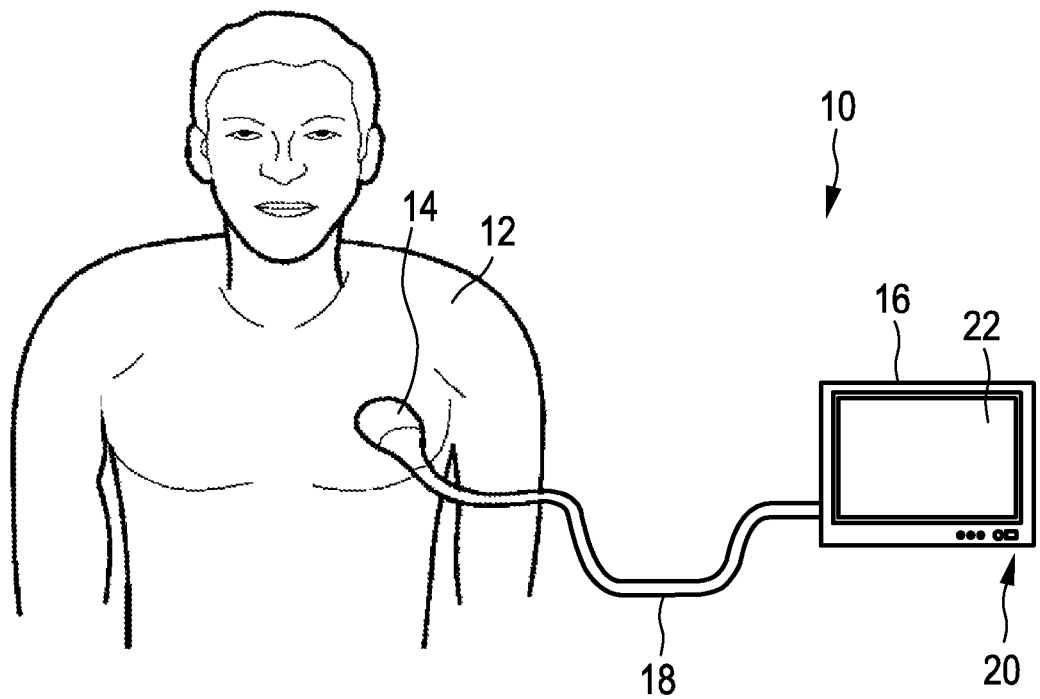
FIG. 1 shows a schematic illustration of an embodiment of an ultrasound assembly.

FIG. 1 illustrates the principle design of an ultrasound transducer assembly, in particular an ultrasound imaging system. This figure is used to explain the background and the working principle of ultrasound systems. It shall be understood that the claimed ultrasound transducer assembly as well as the claimed ultrasound imaging unit are not restricted to such kind of systems.

The ultrasound transducer assembly in FIG. 1 is generally noted with reference numeral 10. The ultrasound transducer assembly 10 is used for scanning an area or a volume of a patient's body 12. It is to be understood that the ultrasound transducer assembly 10 may also be used for scanning other areas or volumes, e.g. body parts of animals or other living beings.

For scanning the patient's body 12 an ultrasound transducer 14 may be provided. In the embodiment shown in FIG. 1, the ultrasound transducer 14 is connected to an ultrasound main frame 16 as a console device. The main frame 16 is shown in FIG. 1 as a mobile console. The main frame 16 may, however, also be formed as a stationary device. The main frame 16 is connected to the ultrasound transducer 14 via an interface 18 formed in a wired manner. Further, it is contemplated that the main frame 16 may also be connected to the ultrasound transducer in a wireless manner, for example using UWB transmission technology. The main frame may further comprise an input device 20. The input device 20 may have buttons, a key pad and/or a touch screen to provide an input mechanism to a user of the ultrasound transducer assembly 10. Additionally or alternatively, other mechanisms may be present in the input device 20 to enable a user to control the ultrasound imaging system 10.

Further, the main frame 16 comprises a display 22 to display data generated by the ultrasound transducer assembly 10 to the user. By this, the volume within the patient's body 12 that is scanned via the ultrasound transducer 14 can be viewed on the display 22 of the main frame 16 by the user of the ultrasound transducer assembly 10.

Figure 2A:
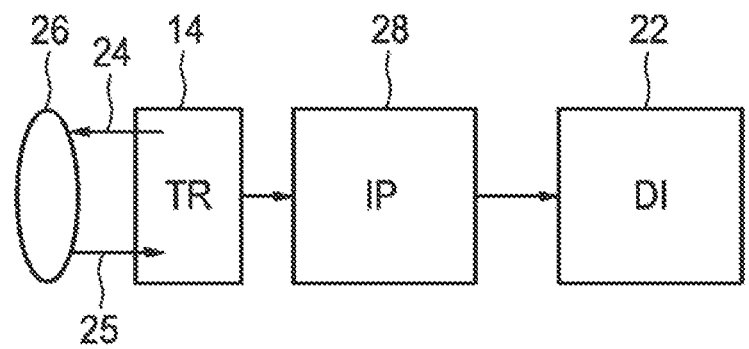
FIG. 2a shows a block diagram that schematically illustrates the processing of signals and data in the ultrasound transducer assembly.

FIG. 2a shows a block diagram illustrating a typical operation of a two-dimensional or three-dimensional ultrasound imaging unit 10. The ultrasound transducer 14 emits ultrasound waves 24 which generate a response 25 from a volume 26 of the patient's body 12 back to the transducer 14. The received signals from the volume 26 are transformed by the transducer 14 into electrical signals. These electrical signals are provided to an image processor 28. The image processor 28 generates image data from the detected acoustic data received from the ultrasound transducer 14. The image processor 28 converts the image data into display data to be displayed on the display 22. The image processor 28 may prepare two-dimensional topographic slices of the volume 26 to be displayed or may convert or render the image data into a three-dimensional image that is displayed on the display 22.

Figure 2B:
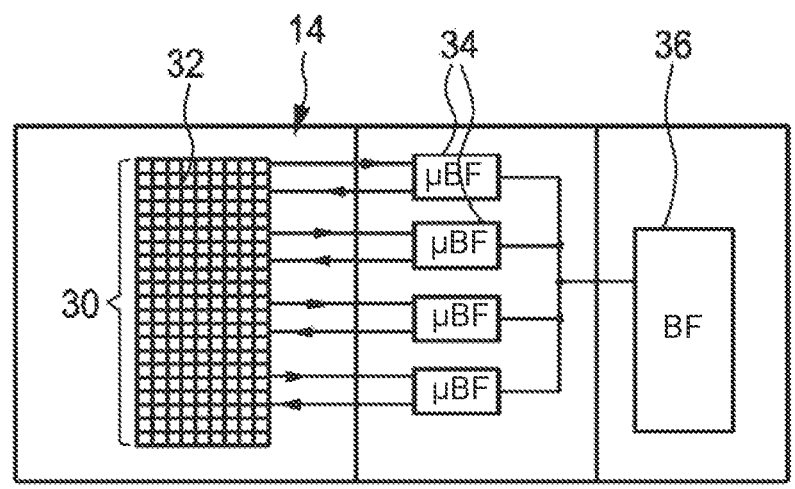
FIG. 2b shows an example of a schematic detailed view of a transducer array and a beam former.

FIG. 2b is a schematic detailed view of the ultrasound transducer 14. The ultrasound transducer 14 comprises an ultrasound transducer array 30, which is formed of a plurality of acoustic elements, which are herein denoted as transducer elements 32. According to the present invention, these transducer elements 32 are formed as capacitive micro-machined ultrasound transducer (CMUT) cells, which are arranged in a matrix to form the transducer array 30. The transducer array 30 is connected to micro-beam formers 34 for beam forming and the micro-beam formers 34 are connected to a main beam former 36, which drives the micro-beam formers 34. The transducer elements 32 transmit the ultrasound signals 24 and receive the generated responses 25. The transducer array 30 may comprise thousands of transducer elements 32 forming a multitude of sub-arrays.

Figure 3A:
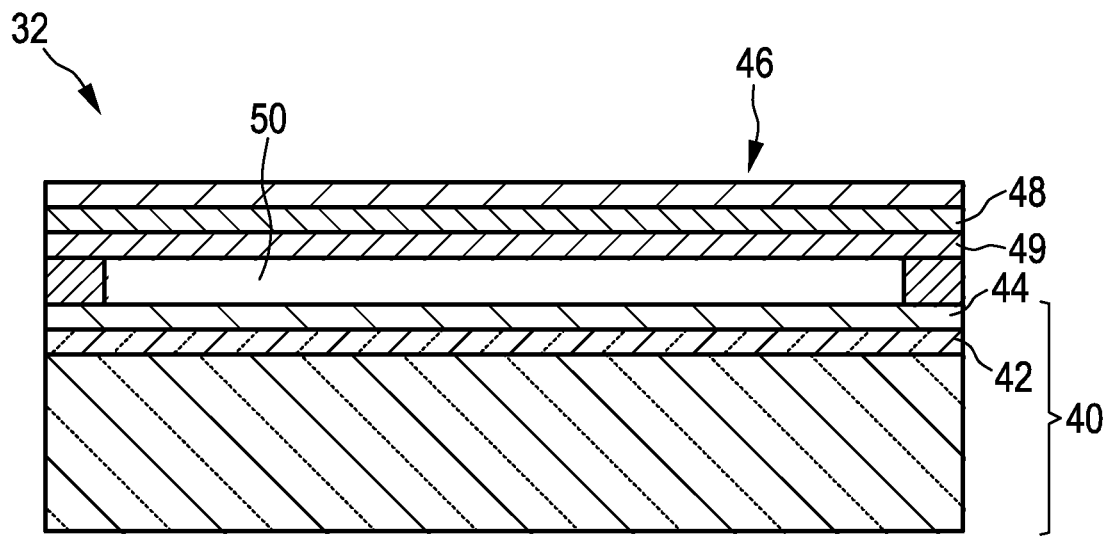
FIG. 3a, b show a schematic cross-sectional view of a capacitive micro-machined transducer cell in a non-collapsed mode and in a collapsed mode.
Figure 3B:
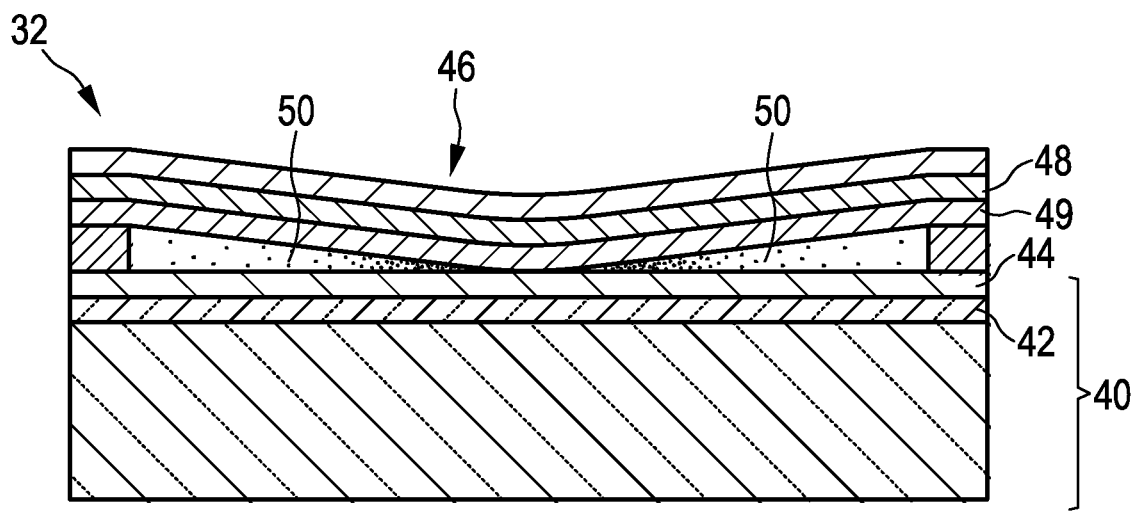

FIGS. 3a and 3b show cross-sectional views of a capacitive micro-machined transducer element 32. The transducer element 32 comprises a substrate 40 comprising a first (bottom) electrode 42 covered by a dielectric layer 44. The transducer element 32 further comprises a flexible membrane 46 comprising a second (top) electrode 48 and a dielectric layer 49 for insulating the electrode 48. The flexible membrane 46 is disposed in a distance to the dielectric layer 44 so that a cavity 50 is formed between the substrate 40 and the membrane 46. The dielectric layer is preferably an oxide layer and most preferred a silicon oxide layer formed on the silicon substrate 40.

For transmitting ultrasound waves 24, an electrical signal is supplied to the electrodes 42, 48 to cause the membrane 46 to move or to vibrate. For receiving ultrasound waves, the membrane 46 is caused by the ultrasound waves 25 to move or vibrate so that the variation of the capacitance between the electrodes 42, 48 can be detected and a corresponding electrical signal can be formed.

In FIG. 3b a cross-sectional view of the transducer element 32 is schematically shown in a collapse mode. In the collapse mode, a DC bias voltage is applied to the electrodes 42, 48 so that the membrane 46 is brought into contact with the surface of the dielectric layer 44 of the substrate 40. In this collapse mode, the sensitivity of the transducer element 32 is significantly increased. Since the electrode 48 is in contact to the dielectric layer 44 a leakage current through the dielectric layer 44 may lead to a breakdown of the dielectric layer 44 if a conductive path is formed through the dielectric layer 44. The reasons for such a dielectric breakdown are intrinsic degradation during the device operation due to a high electric field causing injection of electrons or extrinsic degradation due to defects in the dielectric layer 44 caused during the processing.

The time to breakdown of the dielectric layer 44 and the dielectric layer 49 can be used to estimate a total life time of the transducer array 30 under DC bias voltage. The dielectric lifetime is inversely related to the DC bias voltage and the total time under bias.

Hence, the life time of the transducer array 30 can be increased by reducing the time under bias by actively disconnecting the DC bias voltage from the transducer elements 32 whenever possible during those dead times of the transducer array 30 as described in the following.

Figure 4:
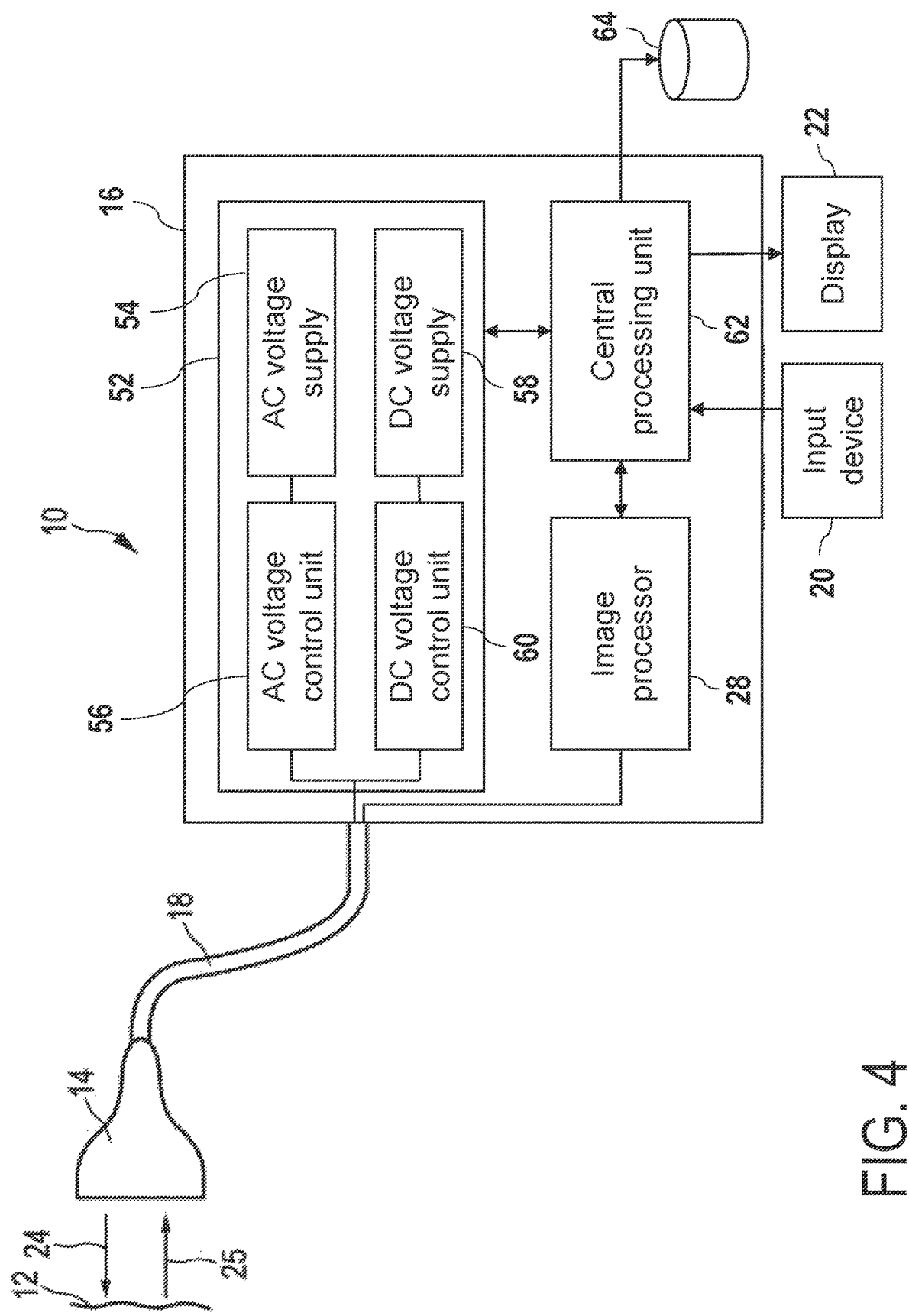
FIG. 4 shows a schematic illustration of the transducer assembly.

FIG. 4 shows a schematic block diagram of the transducer assembly 10. Identical elements are denoted by identical reference numerals, wherein here merely the differences are explained in detail.

The main frame 16 comprises a driver device 52 for driving the transducer elements 32 of the transducer array 30 in the ultrasound transducer 14. The driver device comprises an AC voltage supply 54 and an AC voltage control unit for controlling the AC voltage provided to the transducer elements 32 for emitting the ultrasound waves 24. The driver device 52 further comprises a DC voltage supply 58 and a DC voltage control unit 60 for providing the DC voltage $V_{DC}$ to the transducer elements 32 in order to bring the membrane 46 into contact with the substrate 40 to operate the transducer elements 32 in the collapse mode.

The main frame 16 also comprises the image processor 28 connected to the transducer array 30 in order to form image data from the detected acoustic signals and to provide the image data to the display 22. The main frame 16 further comprises a central processing unit 62 connected to the driver device 52, the image processor 28, the input device 20 and the display device 22. The central processing unit is provided to control the driver device 52 and the image processor 28.

The DC voltage control unit 60 switches the DC voltage provided by the DC voltage supply 58 off or disconnects the DC voltage supply 58 from the transducer elements 32 in order to limit or interrupt the collapse mode of the transducer elements 32. The DC voltage control unit 60 disconnects the DC voltage supply 58 from the transducer elements 32 during a dead time of the transducer elements 32, e.g. between transmitting of the ultrasound waves 24 and receiving of the ultrasound waves 25. The DC voltage may be disconnected when the central processing unit 62 stores image data in a memory 64 or while control data is downloaded, e.g. from the input device 20 such as digital beam forming data, steering data or set-up data which is used by the driver device 52 for driving the transducer array 30.

In a further embodiment, the time duration of the collapse mode is measured and limited to a predefined time period so that the duration of the contact of the flexible membrane 46 to the substrate is limited. In a further embodiment, the temperature of the transducer elements 32 is measured or estimated and the collapse mode is switched off or interrupted when the temperature of the transducer elements 32 reaches a predefined temperature. In a further embodiment, a temperature of the volume 26 of the patient's body 12 is calculated or estimated and the collapse mode is switched off or interrupted when a predefined temperature of the volume 26 is reached.

In a further embodiment, a contact sensor (not shown) senses whether the transducer 14 is in contact to the patients body 12 or to the volume 26 to be measured and the DC voltage control unit 60 disconnects the DC voltage from the transducer elements 32 if the transducer 14 is not in contact to the patients body 12 or the volume 26 to be measured. The contact sensor may be a pressure sensor or may measure the contract ultrasonically.

In a further embodiment, and the DC voltage control unit 60 disconnects the DC voltage from the transducer elements 32 when the input device 20 does not receive input signals for a predefined time period. In other words, the ultrasound transducer 10 switches in a stand-by mode or a freeze mode, in which the collapse mode is switched off after a predefined time period without control signals.

In a further embodiment, the transducer 14 comprises a plurality of transducer units or transducer arrays 30. In this case, the DC voltage control unit 60 disconnects the DC voltage from the transducer elements 32 when the respective transducer unit or transducer array 30 is not in use or de-selected in order to limit the collapse mode.

Figure 5:
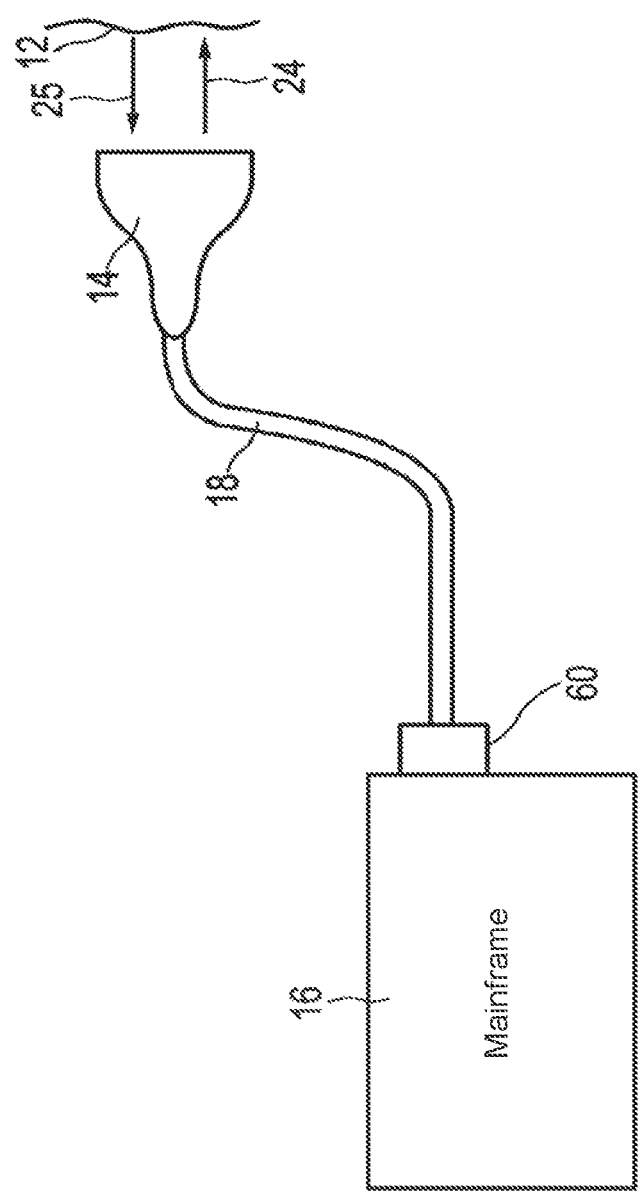
FIG. 5 shows an embodiment of the ultrasound transducer assembly.

FIG. 5 shows a schematic drawing of an embodiment of the transducer assembly 10. Identical elements are denoted by the identical reference numerals, wherein here merely the differences are explained in detail. The DC voltage control unit 60 in this embodiment is disposed as a connector between the main frame 16 and the interface 18 or the connection wire 18 so that the DC voltage control unit 60 forms a connector between the DC voltage supply 58 and the connection wire 18 connecting the ultrasound transducer 14 to the main frame 16. Hence, the DC voltage control unit 60 can easily disconnect the DC voltage $V_{DC}$ in order to interrupt the collapse mode. In this embodiment, the DC voltage control unit 60 can be easily provided as a retrofit equipment or an add-on kit connected between the wire connection 18 and the main frame 16, e.g. by means of corresponding plug connections.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. An ultrasound transducer assembly comprising:
a plurality of transducer elements for transmitting and receiving ultrasound waves each having a substrate and a flexible membrane disposed a distance from the substrate,
an AC voltage control unit for controlling an AC voltage provided to each of the transducer elements,
a DC voltage control unit for controlling a DC bias voltage provided to the transducer elements in order to bring the flexible membranes in a collapse mode into contact with the substrate,
wherein, during operation of the ultrasound transducer assembly for an imaging scan, the DC voltage control unit is configured to change the flexible membranes between the collapse mode and an uncollapsed mode such that:
during a transmission time period of the imaging scan, the plurality of transducer elements emits, in the collapse mode, ultrasound waves into a patient volume,
during a response time period of the imaging scan, the plurality of transducer elements receives, in the collapse mode, an ultrasound response from the patient volume based on the ultrasound waves emitted during the transmission time period, and
during a dead time period of the imaging scan between the transmission time period and the response time period, the plurality of transducer elements is in the uncollapsed mode, to limit a duration the plurality of transducer elements is in the collapse mode during the imaging scan.

2. An ultrasound transducer assembly as claimed in claim 1, further comprising a transducer including the transducer elements and a main frame including a DC voltage supply.

3. An ultrasound transducer assembly as claimed in claim 2, wherein the DC voltage control unit is integrated in a connector connecting the main frame and the transducer.

4. An ultrasound transducer assembly as claimed in claim 2, wherein the DC voltage control unit is integrated in the main frame.

5. An ultrasound transducer assembly as claimed in claim 1, wherein the transducer elements are arranged in an array of transducer elements, and wherein the array is controlled by a control unit for ultrasound imaging.

6. An ultrasound transducer assembly as claimed in claim 5, wherein during a second dead time period, while the control unit for ultrasound imaging stores image data received from the array, the plurality of transducer elements is in the uncollapsed mode, to limit a duration the plurality of transducer elements is in the collapse mode during the imaging scan.

7. An ultrasound transducer assembly as claimed in claim 5, wherein during a second dead time period, while the control unit for ultrasound imaging receives data for controlling the array, the plurality of transducer elements is in the uncollapsed mode, to limit a duration the plurality of transducer elements is in the collapse mode during the imaging scan.

8. An ultrasound imaging unit comprising an ultrasound transducer assembly as claimed in claim 1.

9. An ultrasound imaging unit as claimed in claim 1, wherein the DC voltage control unit is configured to change the flexible membranes to the uncollapsed mode by disconnecting the DC bias voltage from the transducer elements.

10. An ultrasound transducer assembly as claimed in claim 1, wherein during a second dead time period, between receipt of an ultrasonic wave by the ultrasound transducer assembly in a receiving mode and transmission of an ultrasonic wave by the ultrasound transducer assembly in a transmission mode, the plurality of transducer elements is in the uncollapsed mode, to limit a duration the plurality of transducer elements is in the collapse mode during the imaging scan.

11. An ultrasound transducer assembly as claimed in claim 1, wherein during a second dead time period, when a temperature of the ultrasound transducer assembly exceeds a predefined value, the plurality of transducer elements is in the uncollapsed mode, to limit a duration the plurality of transducer elements is in the collapse mode during the imaging scan.

12. An ultrasound transducer assembly as claimed in claim 1, wherein during a second dead time period, when the transducer assembly is not in contact with a patient's body, the plurality of transducer elements is in the uncollapsed mode, to limit a duration the plurality of transducer elements is in the collapse mode during the imaging scan.

13. An ultrasound transducer assembly as claimed in claim 1, wherein during a second dead time period, when at least one of the ultrasound transducer assembly or a control unit for ultrasound imaging is sending or receiving data, the plurality of transducer elements is in the uncollapsed mode, to limit a duration the plurality of transducer elements is in the collapse mode during the imaging scan.

14. An ultrasound transducer assembly as claimed in claim 1, wherein during a second dead time period, after a predefined control signal free time period, the plurality of transducer elements is in the uncollapsed mode, to limit a duration the plurality of transducer elements is in the collapse mode during the imaging scan.

15. A method for transmitting and receiving ultrasound waves by an ultrasound transducer assembly, comprising the steps of:
   providing an AC voltage to a plurality of transducer elements each having a substrate and a flexible membrane disposed a distance to the substrate,
   providing a DC bias voltage to the plurality of transducer elements in order to bring the flexible membranes in a collapse mode into contact with the substrate, and
   during operation of the ultrasound transducer assembly for an imaging scan, changing the flexible membranes between the collapse mode and an uncollapsed mode such that:
      during a transmission time period of the imaging scan, the plurality of transducer elements emits, in the collapse mode, ultrasound waves into a patient volume in the collapse mode,
      during a response time period of the imaging scan, the plurality of transducer elements receives, in the collapse mode, an ultrasound response from the patient volume based on the ultrasound waves emitted during the transmission time period, and
      during a dead time period of the imaging scan between the transmission time period and the response time period, the plurality of transducer elements is in the uncollapsed mode, to limit a duration the plurality of transducer elements is in the collapse mode during the imaging scan.

16. A method as claimed in claim 15, wherein changing the flexible membranes to the uncollapsed mode comprises disconnecting the DC bias voltage from the transducer elements.

17. A method as claimed in claim 15, wherein during a second dead time period, during a predefined control signal free time period, the plurality of transducer elements is in the uncollapsed mode, to limit a duration the plurality of transducer elements is in the collapse mode during the imaging scan.

* * * * *